United States Patent [19]

Roth et al.

[11] Patent Number: 5,620,964

[45] Date of Patent: Apr. 15, 1997

[54] COMPOSITIONS FOR TREATING AND INHIBITING GASTRIC AND DUODENAL ULCERS

[75] Inventors: Stephen Roth, Gladwyne; Edward J. McGuire, Furlong, both of Pa.; Dennis H. Langer, Princeton, N.J.

[73] Assignee: Neose Technologies, Inc., Horsham, Pa.

[21] Appl. No.: 461,000

[22] Filed: Jun. 5, 1995

Related U.S. Application Data

[63] Continuation of Ser. No. 104,483, Jul. 28, 1993, abandoned, which is a continuation-in-part of Ser. No. 922,519, Jul. 31, 1992, abandoned.

[51] Int. Cl.$^6$ .................................................. A61K 31/715
[52] U.S. Cl. ................................ 514/53; 514/42; 514/54; 514/58; 514/61; 514/925; 514/926; 514/927
[58] Field of Search .............................. 514/42, 53, 58, 514/61, 925, 926, 927, 54

[56] References Cited

U.S. PATENT DOCUMENTS

| | | | |
|---|---|---|---|
| 4,935,406 | 6/1990 | Colmena et al. | 514/54 |
| 4,938,967 | 7/1990 | Newton et al. | 424/458 |
| 5,318,780 | 6/1994 | Viegas et al. | 424/427 |

OTHER PUBLICATIONS

Boren et al., Science, vol. 262, 1892–1895 17 Dec. 1993.
Evans et al., Journal of Bacteriology, Feb. 1993, pp. 674–683, vol. 15, No. 3.
Saitoh et al., Federation of European Biochemical Societies, May 1991, vol. 282, No. 2 385–387.
Lingwood, et al., *Infection and Immunity*, Jul. 1993, pp. 2474–2478, vol. 61, No. 6.
Fauchere, et al., *Microbial Pathogenesis* 1990: 9: 427–439.
Lingwood, et al., *Infection and Immunity*, Jun. 1992, pp. 2470–2474, vol. 60, No. 6.
Robinson, et al., *J. Med. Microbiol.*, vol. 33 (1990). 277–284, 1990 The Pathological Society of Great Britain and Ireland.
Figueroa, et al., Journal of Infection (1992) 24,263–267.
Talley, et al., Journal of the National Cancer Institute (1991) 83, 1734–1739.
Wotherspoon, et al., *The Lancet*, vol. 342, Sep. 4, 1993, pp. 575–577.
Russell, et al., *The Lancet*, vol. 342, Sep. 4, 1993, pp. 571–574.
National Institutes of Health, Concensus Development Conference Statement, *Helicobacter pylori in Peptic Ulcer Disease*, Feb. 7–9, 1994, 19 pages.
Falk, et al., *Proc. Natl. Acad. Sci, USA*, vol. 90 pp. 2035–2039, Mar. 1993.
Huang, et al., *Journal of General Microbiology* (1992), 138, 1503–1513.
Koybayashi et al., Infection and Immunity, Oct. 1993, pp. 4058–4063. vol. 61, No. 10.
Clyde, et al., Infection and Immunity, Oct. 1993, pp. 4058–4063, vol. 61, No. 10.
Podolsky, J. of Biological Chemistry vol. 260, No. 14, pp. 8262–8271.
Evans, et al., Infection and Immunity(1988) 56: 2896–2906.
Evans, et al., Infection and Immunity(1989) 57: 2272–2278.
Lingwood, et al., The Lancet(1989) 2: 238–241.

(List continued on next page.)

*Primary Examiner*—John W. Rollins
*Assistant Examiner*—Francisco C. Prats

[57] ABSTRACT

A composition for treating and/or inhibiting gastric and duodenal ulcers, comprising an oligosaccharide selected from the group consisting of Formula I

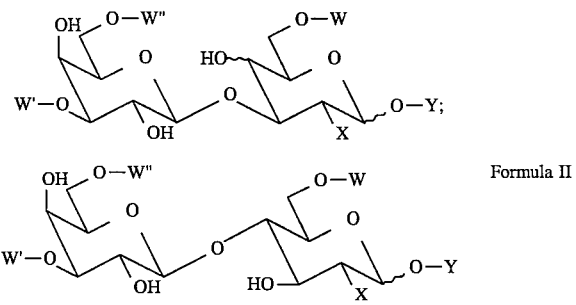

or a mixture thereof;
wherein:
  X is independently OH or NHAc;
  Y is independently H, or an amino acid or a peptide of 2–100, preferably 2–20, amino acids; and
  W, W', and W" are each independently H or

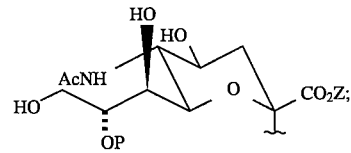

where Z is independently H or a pharmaceutically acceptable cation; and
  P is independently H or

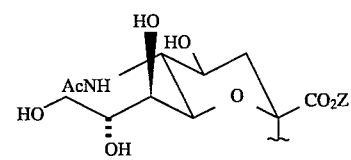

where Z is defined as above;
  wherein at least one of W, W' or W" is an α-N-acetylneuraminic acid moiety, and
  wherein W' and W" are not simultaneously α-N-acetylneuraminic acid moiety
  with the proviso that the compound of Formula II is not NAN α(2→3)Gal β1-4 Glu or NAN α(2→6)Gal β1-4 Glu; and a kit for detecting the presence of *Helicobacter pylori* comprising at least one compound of the Formula I or II, are described.

19 Claims, No Drawings

OTHER PUBLICATIONS

Tzouvelekis, et al., Infection and Immunity(1991) 59:4252–4254.

Lambert, Reviews of Infectious Diseases(1991) 13 (Suppl.8):S691–5.

Dunn, et al., Reviews of Infectious Diseases(1991) 13 (Suppl.8):S657–64.

Hayes et al, J. Biological Chemistry, 254 (18):8777–8780, (1979).

Mizuochi et al, J. Biological Chemistry, 255(8):3526–3531, (1980).

Kessler et al, J. Biological Chemistry, 254(16):7909–7914, (1979).

Spiro et al, J. Biological Chemistry, 249(18):5704–5717, (1974).

Pelczar et al, Elements of Microbiology, McGraw–Hill Book Company:New York, 1981, pp. 222–223.

COMPOSITIONS FOR TREATING AND INHIBITING GASTRIC AND DUODENAL ULCERS

RELATED APPLICATIONS

This application is a continuation of application Ser. No. 08/104,483, filed on Jul. 28, 1993, abandoned, which is a Continuation-in-Part of Ser. No. 07/922,519, filed on Jul. 31, 1992, abandoned.

BACKGROUND OF THE INVENTION

1. Field of the Invention

The present invention relates to compounds and compositions for treating and inhibiting gastric and duodenal ulcers, and to methods of treating and inhibiting gastric and duodenal ulcers.

2. Discussion of the Background

Infection by the gram-negative, spiral, microaerophilic bacterium *Helicobacter pylori* (*H. pylori*), formerly known as *Campylobactor pylori* (*C. pylori*), is a primary cause of non-autoimmune gastritis, is a factor in peptic ulcer disease and is more common in patients with gastric carcinoma. First isolated by Warren (*Lancet* (1983) 1:1273) and Marshal (*Lancet* (1983) 1:1273–5), *H. pylori* has been isolated in gastric tissue biopsies in patients throughout the world. While the precise mechanism of inflammation is not well understood, *H. pylori* is found in association with the apical surfaces of gastric mucous-secreting cells.

Due to the site specificity of attachment, it has been suggested that there are specific attachment sites for *H. pylori* which exist on gastric and duodenal mucous-secreting cells. Numerous studies have been undertaken to attempt to identify the specific binding site of *H. pylori*.

Evans et al (*Infection and Immunity* (1988) 56:2896–2906) reported that *H. pylori* binding to an erythrocyte receptor is preferentially inhibited by N-acetylneuraminyl-α(2→3)-Gal β1→4 Glc [NeuAc(2→3)-lactose] as compared with NeuAc(2→6)-lactose. Sialoproteins which contain the NeuAc(2→3)Gal isomer of NeuAc-lactose, i.e., human erythrocyte glycophorin A, fetuin, and human $α_2$-macroglobulin, also inhibited *H. pylori* binding, but at much higher concentrations (mg/ml) than that observed for NeuAc(2→3)-lactose, while no inhibition was observed for the corresponding asialoproteins.

These researchers further observed that NeuAc-lactose (also called sialyllactose) containing primarily the NeuAc(2→6)Gal isomer showed no inhibition of binding, leading the researchers to conclude that the receptor on the erythrocytes is a sialoprotein containing NeuAc(2→3)Gal. Although the NeuAc(2→3)Gal moiety, which Evans et al believed to be the specific site of binding for *H. pylori*, is a structure which occurs widely in nature, they rationalized the selective binding of *H. pylori* to be due to the unique gastrointestinal environment. This, in their view, accounts for the lack of further colonization by *H. pylori*.

Evans et al (*Infection and Immunity* (1989) 57:2272–2278) have also observed that *H. pylori* binds to monolayers of Y-1 mouse adrenal cells. But, this adherence can be prevented by pretreating the Y-1 cells with neuraminidase and is blocked by sialyllactose-containing fetuin.

Lingwood et al (*Lancet* (1989) 2:238–241) have reported the isolation of a gastric glycerolipid material which they observed to behave as a receptor for *H. pylori*. The material was isolated from red blood cells, and mucosal scrapings of pig stomach and human stomach. The investigators postulated that the material was a sulphated alkylacylglycerolipid, but the actual structure of this material was not been reported. Subsequent investigations (Lingwood et al., *Infection and Immunity* (1992) 60:2470–2474) showed that this receptor is phospatidylethanolamine.

Tzovelekis et al (*Infection and Immunity* (1991) 59:4252–4253) reported binding inhibition of *H. pylori* to HEp-2 cells by gastric mucin. The investigators observed that purified mucin showed the greatest inhibition of *H. pylori* binding while asialomucin exhibits somewhat diminished inhibition and periodate-oxidized mucin exhibited the lowest level of binding. On these observations, the researchers concluded that sialic acids are at least partially responsible for the binding interaction between *H. pylori* and human gastric mucin.

Thus the binding inhibition studies all point to a *H. pylori* binding specific receptor which possesses an N-acetylneuraminic acid (sialic acid) (Tzouvelekis et al and Evans et al) bound in a 2→3 manner to a lactose (Evans et al ).

In addition to the numerous binding inhibition studies, methods have been pursued to treat gastric and duodenal ulcer patients. Colloidal bismuth subcitrate (CBS) has been used successfully in treating both gastric and duodenal ulcer diseases (for a review, see Lambert in *Reviews of Infectious Diseases* (1991) 13 (Suppl. 8):S691–5. CBS has proven effective as a histamine H2 antagonist and has been associated with lower relapse rates after cessation of therapy attributed to CBS's ability to eradicate *H. pylori*. Bismuth subsalicylate (BSS) has also been observed to inhibit *H. pylori*.

Additional studies in eliminating *H. pylori* have been conducted using the proton pump inhibitor, omeprazole.

Coleman et al (U.S. Pat. No. 4,935,406) reported a method for relieving gastrointestinal disorder, resulting from *H. pylori* population, through the administration of bismuth (phosph/sulf)ated saccharide compositions. The saccharide compositions according to this method are simple phosphates and sulfates of aldose and ketose monosaccharides.

Clinical trials have been reported (Evans et al, *Ann. Internal Med.* (1991) Aug. 15, 115(4):266–9) in treating *H. pylori* using ranitidine in conjunction with a "triple therapy" of amoxicillin or tetracycline, metronidazole (an antiprotozoal), and BSS. The clinical studies suggested that ulcer healing was more rapid in patients receiving ranitidine plus the "triple therapy" than in patients receiving ranitidine alone.

However, long-term eradication of this organism has been difficult with these therapies. The antibiotic approach runs the risk of the development of new antibiotic resistant strains. Thus, a method of treating *H. pylori* with good long-term eradication has not yet been developed.

SUMMARY OF THE INVENTION

Accordingly, one object of the present invention is to provide novel compositions and methods for inhibiting and/or treating gastric and/or duodenal ulcers.

Another object of the present invention is to provide a method for inhibiting the adhesion of *Helicobacter pylori* to mammalian tissue, including eliminating *Helicobacter pylori* from the stomach and/or duodenum of a in need thereof patient.

Another object of the present invention is to provide a kit for detecting the presence of *Helicobacter pylori* in a sample.

All of the above objects of the present invention and other objects which are apparent from the description of the invention given herein below have been discovered by the inventors to be satisfied by a composition comprising an oligosaccharide selected from the group consisting of Formula

[Structure of Formula I]

[Structure of Formula II]

or a mixture thereof;
wherein:

X is independently OH or NHAc;

Y is independently H, or an amino acid or a peptide of 2–100, preferably 2–20, amino acids; and W, W', and W" are each independently H or

[Structure showing sialic acid derivative with $CO_2Z$ and OP]

where Z is independently H or a pharmaceutically acceptable cation; and

P is independently H or

[Structure showing sialic acid derivative with $CO_2Z$ and OH]

where Z is defined as above;
wherein at least one of W, W' or W" is an α-N-acetylneuraminic acid moiety, and
wherein W' and W" are not simultaneously an α-N-acetylneuraminic acid moiety
with the proviso that the compound of Formula II is not NAN α(2→3)Gal β1-4 Glu or NAN α(2→6)Gal β1-4 Glu.

A composition containing at least one oligosaccharide of Formula I or Formula II alone, or in combination with an H2 blocker, an antibiotic and/or an antiulcerative compound, has been found by the inventors to be effective at inhibiting the binding of *Helicobacter pylori* to the gastric and duodenal mucosa and relieving the effects of gastric and duodenal ulcers.

DETAILED DESCRIPTION OF THE PREFERRED EMBODIMENTS

The following abbreviations are used throughout the text: "GalNAc" for N-Acetylgalactosamine; "Gal" for galactose; "Glc" for glucose; "GlcNAc" for N-Acetylglucosamine; "NAN" or "NeuAc" for N-Acetylneuraminic acid; and "ser" for serine.

In the oligosaccharide of Formula I, the OH group at the 4-position of the sugar on the right side of the molecule represents both the axial and equatorial epimeres. When the OH at the 4-position is in the axial position, then the sugar on the right side of the molecule is a Gal or GalNAc moiety. When the OH at the 4-position is in the equatorial position, then the sugar on the right side of the molecule is a Glc or GlcNAc moiety. Thus the core structure of Formula I represents either a Gal β1-3 Gal, Gal β1-3 GalNAc, Gal β1-3 Glc or Gal β1-3 GlcNAc.

The oligosaccharides according to Formula I of the present invention comprise a core made up of an α-N-acetylneuraminic acid moiety bound via its 2-position to either the 3-position or 6-position of a β-galactose moiety, which, in turn, is bound via its 1-position to the 3-position of a galactose, N-acetylgalactosamine, glucose or N-acetylglucosamine moiety, which is bound via its 6-position to the 2-position of an α-N-acetylneuraminic acid. Alternatively, any of the α-N-acetylneuraminic acid groups, but not all simultaneously, may be replaced with H.

In a preferred embodiment, this core structure further comprises an amino acid bound to the oxygen at the 1-position of the galactose, N-acetylgalactosamine, glucose or N-acetylglucosamine moiety, to provide as shown below an oligosaccharide of Formula I:

[Structure of Formula I]

wherein X is OH or NHAc, Y is serine or threonine, W and W' are each an α-N-acetylneuraminic acid moiety, W" is H and Z is independently H or a known pharmaceutically acceptable cation.

Specifically, the oligosaccharide of Formula I may be Formula Ia

[Structure of Formula Ia]

or Formula Ib

[Structure of Formula Ib]

where X, Y, W, W', W", Z and P are as defined above for Formula I.

In other preferred embodiments, the oligosaccharide of Formula I is selected from the group NANα2-3Galβ1-3(NANα2-6)GalNAc, NANα2-3Galβ1-3(NANα2-6)GalNAcα1-ser, NANα2-3Galβ1-3GalNAc, NANα2-6Galβ1-3(NANα2-6)GalNAc, NANα2-6Galβ1-3(NANα2-6) GalNAcα1-ser, NANα2-6Galβ1-3GalNAc, Galβ1-3(NANα2-6) GalNAc, NANα2-3Galβ1-3(NANα2-6)Gal, NANα2-3Galβ1-3 (NANα2-6)Gal α1-ser, NANα2-3Galβ1-3Gal, NANα2-6Galβ1-3(NANα2-6)Gal, NANα2-6Galβ1-3(NANα2-6)Galα1-ser, NANα2-6Galβ1-3Gal, Galβ1-3(NANα2-6)Gal, NANα2-3Galβ1-3(NANα2-6) GlcNAc, NANα2-3Galβ1-3(NANα2-6) GlcNAcα1-ser, NANα2-3Galβ1-3GlcNAc, NANα2-6Galβ1-3(NANα2-6)GlcNAc, NANα2-6Galβ1-3(NANα2-6) GlcNAcα1-ser, NANα2-6Galβ1-3GlcNAc, Galβ1-3(NANα2-6) GlcNAc, NANα2-3Galβ1-3(NANα2-6)Glc, NANα2-3Galβ1-3(NANα2-6)Glcα1-ser, NANα2-3Galβ1-3Glc, NANα2-6Galβ1-3(NANα2-6)Glc, NANα2-6Galβ1-3 (NANα2-6)Glcα1-ser, NANα2-6Galβ1-3Glc, Galβ1-3(NANα2-6)Glc and a mixture thereof.

The oligosaccharides according to Formula II of the present invention comprise a core made up of an α-N-acetylneuraminic acid moiety bound via its 2-position to either the 3-position or 6-position of a β-galactose moiety, which, in turn, is bound via its 1-position to the 4-position of a glucose or N-acetylglucosamine moiety, which is bound via its 6-position to the 2-position of an α-N-acetylneuraminic acid. Alternatively, any of the α-N-acetylneuraminic acid groups, but not all simultaneously, may be replaced with H. However, the compound of Formula II does not include NAN α(2→3)Gal β1-4 Glu or NAN α(2→6)Gal β1-4 Glu.

In a preferred embodiment, this core structure further comprises an amino acid bound to the oxygen at the 1-position of the glucose or N-acetylglucosamine moiety, to provide as shown below an oligosaccharide of Formula II:

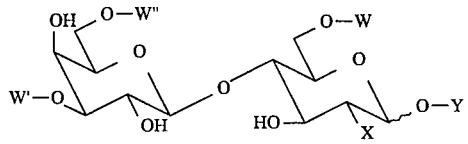

wherein X is OH or NHAc, Y is serine or threonine, W and W' are each an α-N-acetylneuraminic acid moiety and Z is independently H or a known pharmaceutically acceptable cation.

In other preferred embodiments, the oligosaccharide of Formula I is selected from the group NANα2-3Galβ1-4(NANα2-6) GlcNAc, NANα2-3Galβ1-4(NANα2-6)GlcNAcα1-ser, NANα2-3Galβ1-4GlcNAc, NANα2-6Galβ1-4(NANα2-6)GlcNAc, NANα2-6Galβ1-4(NANα2-6)GlcNAcα1-ser, NANα2-6Galβ1-4GlcNAc, Galβ1-4(NANα2-6)GlcNAc, NANα2-3Galβ1-4(NANα2-6)Glc, NANα2-3Galβ1-4(NANα2-6)Glcα1-ser, NANα2-6Galβ1-4(NANα2-6)Glc, NANα2-6Galβ1-4(NANα2-6) Glcα1-ser, Galβ1-4(NANα2-6)Glc and a mixture thereof.

In addition, for the oligosaccharide of Formula I or Formula II the group Y may represent an amino acid or peptide of from 2–100 amino acids, preferably 2–20 amino acids. It is noted that the glycoprotein fetuin, contains a peptide of at least 500 amino acids.

In addition, any one of or all of the free hydroxyl groups on the oligosaccharide of Formula I or Formula II may be acylated with a $C_{1-6}$ acyl group by treatment with a suitable acylating agent such as acetyl chloride, propionyl chloride, butyryl chloride or acetic anhydride.

The α-N-acetylneuraminic acid moieties as they appear in Formula I or II may further be substituted at the 8-position with an α-N-acetylneuraminic acid moiety. Accordingly for all of the above-identified compounds of Formula I and Formula II any of the α-N-acetylneuraminic acid moieties may be replaced by NANα2-8NANα2-. This may be done by treating a mono α-N-acetylneuraminic acid compound of Formula I or II with CMP-NAN and an α-N-acetylneuraminic acid transferase specific for transfer to an α-N-acetylneuraminic acid.

Of the bis sialylated oligosaccharides of the present invention, are for example the bis sialylated compounds of Formula II, NANα2-8NANα2-3Galβ1-4Glc and NANα2-8NANα2-6Galβ1-4Glc.

Any known suitable pharmaceutically acceptable cations may be used with the oligosaccharides of Formula I or Formula II, including the cations of conventional non-toxic salts including a metal salt such as an alkali metal salt (e.g. sodium salt, potassium salt, etc.) or an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N, N'-dibenzylethylenediamine salt, etc.), an organic acid salt (e.g. formate, acetate, trifluoroacetate, maleate, tartrate, methanesulfonate, benzenesulfonate, toluenesulfonate, etc.), an inorganic acid salt (e.g. hydrochloride, hydrobromide, sulfate, phosphate, etc.), a salt with an amino acid (e.g. arginine salt, aspartic acid salt, glutamic acid salt, etc.), and the like.

The structure NANα2-3Galβ1-3(NANα2-6)GalNAc has been identified as an O-linked carbohydrate found in bovine Factor X (Mizvochi et al, *J. Biol. Chem.* (1977) 255:3526), bovine high-molecular weight ininogen (Endo et al, *J. Biochem. Tokyo* (1977) 82:545), human plasminogen, (Hayes et al, *J. Biol. Chem.* (1979) 254:8777), immunoglobulin (Chandraskaren et al, *J. Biol. Chem.*, (1981) 256:1549), the β-subunit of human chorionic gonadotropin, (M. Kessler et al, *J. Biol. Chem.* (1979) 254:7909), bovine fetuin (R. Spiro et al, *J. Biol. Chem.* (1974) 249:5704) and human apolipoprotein C-III (P. Yaith, *Biochem. Biophys. Acta* (1978) 541:234).

The oligosaccharide of the present invention may be obtained using any known method, including (1) enzymatically, using one of the inventor's method described in published international application WO 91/16449, (2) synthetically, using classical organic chemistry, or (3) by degradation of a natural occurring oligosaccharide, glycolipid, or glycopeptide.

The compound NANα2-3Galβ1-3(NANα2-6)GalNAc-itol, wherein the acetal of the terminal GalNAc has been reduced to the primary alcohol, may be obtained by alkaline hydrolysis and $NaBH_4$ reduction of fetuin. Illustrative hydrolysis conditions consist of reacting fetuin in 0.05M NaOH and 1M $NaBH_4$ at 50° C. for 16 h in water.

The compound NANα2-3Galβ1-3(NANα2-6)GalNAc-peptide may be obtained by protease mediated degradation of fetuin in aqueous solution at about 50° C.

However, as a pharmaceutically acceptable source of this compound, the hydrolysis product of fetuin may be disfavored due to the possible presence of mad cow's disease. While purification and treatment techniques can rule out transfer of this virus to the composition, enzymatic synthesis is still preferred.

The present oligosaccharide may be administered in conjunction with a known proton pump inhibitor or a known H2 receptor antagonist. A representative proton pump inhibitor is omeprazole, and representative $H_2$ antagonists include cimetidine, ranitidine, nizatidine and famotidine. The amount of proton pump inhibitor and $H_2$ antagonist administered in conjunction with the present oligosaccharide is about the same amount administered for their known therapy. Accordingly, effective dosages of the proton pump inhibitor and $H_2$ can be determined by routine experimentation.

Alternatively a known antiulcerative compound may be used in conjunction with or as a replacement for the H2 receptor antagonist. Suitable antiulceratives include aceglutamide aluminum complex, ε-acetamidocaproic acid zinc salt, acetoxolone, arbaprostil, benexate hydrochloride, bismuth subcitrate sol, carbenoxolone, cetraxate, cimetidine, enprostil, esaprazole, famotidine, ftaxidide, gefarnate, guaiazulene, irsogladine, misoprostol, nazatidine, ornoprostil, γ-oryzanol, pifarnine, pirenzepine, plaunotol, ranitidine, rioprostil, rosaprostol, rotraxate, roxatidine acetate, sofalcone, spizofurone, sucralfate, teprenone, trimoprostil, trithiozine, troxipide, and zolimidine. The amount of antiulcerative administered in conjunction with the present oligosaccharide is about the same amount administered for its known therapy. Accordingly, effective dosage of the antiulcerative can be determined by routine experimentation.

Alternatively, the present oligosaccharide may be administered in conjunction with an antibiotic with activity against *H. pylori*. Suitable antibiotics include metronidazole, tetracycline, bismuth, erythromycin, macrolide, quinoline and amoxicillin. The amount of antibiotic administered in conjunction with the present oligosaccharide is about the same amount administered for its known therapy. Accordingly, effective dosage of the antibiotic can be determined by routine experimentation.

The anti-*H. pylori* compositions of the present invention contains one or a plurality of oligosaccharides of Formula I or Formula II in association with any suitable liquid or solid, pharmaceutically acceptable carrier or excipient, preferable in a form suitable for oral or enteral administration. In addition, the anti-*H. pylori* compositions of the present invention are preferably pyrogen free.

The anti-*H. pylori* compositions are usually administered as a mixture with a carrier suitably selected depending upon the route for administration using standard formulations. For example, the compound of the present invention may be administered in the form of tablets which may be prepared using known techniques by adding to a powder of the active ingredient of the present invention an excipient such as starch, lactose, sucrose, glucose, crystalline cellulose, calcium carbonate or kaolin, a hydroxypropylcellulose, a glucose solution, a sucrose solution, water or ethanol, a disintegrator such as starch, agar, gelatin powder, carboxymethylcellulose calcium (CMC-Ca), carboxymethylcellulose sodium (CMC-Na), crystalline cellulose, calcium carbonate or sodium hydrogencarbonate, or a lubricant such as magnesium stearate, calcium stearate, talc, macrogoal 4,000, macrogoal 6,000 or stearic acid.

The mixture is then subjected to compression molding by a conventional tableting method, and if necessary, applying a sugar coating by means of a concentrated sugar solution containing e.g. gum arabic, talc, polyvinylpyrrolidone, polyethyleneglycol and/or titanium oxide, applying a film coating by means of a film-forming agent composed of e.g. polyvinyl acetal diethylaminoacetate, hydroxypropylmethylcellulose, hydroxypropylcellulose, ethylcellulose or polyvinylpyrrolidone or applying an enteric coating by means of a film-forming agent composed of e.g. ethylcellulose phthalate, cellulose acetate phthalate or hydroxypropylmethylcellulose phthalate.

These pharmaceutical compositions may be in the form of granules or fine granules which may be prepared by adding to the active ingredient of the present invention a binder such as starch, gelatin, gum arabic, methylcellulose, sodium carboxymethylcellulose, heavy silicic anhydride or light silicic anhydride, followed by kneading and granulation by usual methods; or as a powder of the active ingredient of the present invention by itself; or as capsules which may be prepared by adding to the active ingredient of the present invention an excipient such as lactose, starch or crystalline cellulose and/or a lubricant such as magnesium stearate, calcium stearate or talc, and filling the mixture into capsules.

A solution or suspension may be prepared by adding any diluent customarily, used in the art. For example, suitable diluents include water, ethyl alcohol, propylene glycol, polyoxyethylene sorbitol, and sorbitan esters. Sodium chloride, glucose or glycerol may be incorporated into such a liquid preparation in an amount sufficient to prepare an isotonic solution. The therapeutic composition may also further contain ordinary dissolving aids, buffers, pain-alleviating agents, art preservatives, and optionally coloring agents, fragrances, flavors, sweeteners and other pharmacologically active agents such are well known in the art.

Suitable compositions may take the form of a solution, suspension, tablet, coated tablet or any pharmaceutically acceptable form suitable for delivery to the stomach or duodenum.

According to a preferred embodiment of the present invention, the oligosaccharide or anti-*H. pylori* compositions are administered enterally to a patient in need thereof to inhibit *H. pylori* binding or eliminate *H. pylori* colonies from the patient's stomach and/or duodenum.

Typically, suitable patients are humans. However the present method is also applicable to treatment of animals, including but not limited to mammals such as cows, horses, sheep, goats, dogs, cats, rodents and non-human primates, fowl such a chickens, turkeys and ducks, and fish.

Suitable amounts of the composition to be administered include those which produce an effective stomach concentration of oligosaccharide of from 1 μg to 10,000 mg/ml per dose, preferably 100 to 1000 μg/ml. When a proton pump inhibitor, H2 antagonist, or antiulcerative is coadministered, the composition is formulated to provide between 10–500 mg, preferably 100–300 mg of the proton pump inhibitor, H2 antagonist, or antiulcerative daily. Dosage forms include such unit dosage forms such as tablets, capsules, solutions or suspensions.

In another embodiment of this invention the oligosaccharide of Formula I or Formula II is provided as a multivalent molecule. In this embodiment, at least one type of the oligosaccharide of Formula I or Formula II is bound to a polymer using known techniques so as to produce a polymer to which more than one individual molecules of the oligosaccharide of Formula I or Formula II are covalently attached. The polymer backbone is sufficiently long to provide a multivalent molecule leaving from between 2–1, 000, preferably 10–100, more preferably 20–30 molecules of the compound of Formula I or Formula II bound to the polymer.

The oligosaccharide of Formula I or Formula II is preferably bound to the polymer via the free anomeric carbon of the galactose, N-acetylgalactosamine, glucose or N-acetylglucosamine moiety of Formula I or the glucose or N-acetylglucosamine moiety of Formula II when Y=H, or the peptide when Y=peptide. Suitable polymers are any polymer material which may be reacted with the anomeric carbon of a saccharide, such as a polylysine, a polyacrylamide or a cyclodextrin.

For example, the oligosaccharide of Formula I or Formula II may be bound to a support to form a bead wherein the surface of the bead is bound with the compound of Formula I or Formula II.

Another embodiment of this invention, which relates to one of the inventor's application Ser. No. 07/241,012, filed Sep. 2, 1988, provides a kit for detecting *H. pylori*. The kit is analogous to a kit for performing ELISAs, but uses a compound of Formula I or Formula II which is bound to a solid support, instead of the antigens or antibodies bound to solid supports normally found with ELISA kits. The kit comprises a container, and contained therein, the compound of Formula I or Formula II bound to a solid support. The compound of Formula I or Formula II is bound to a polymer support through the anomeric carbon of the galactose, N-acetylgalactosamine, glucose or N-acetylglucosamine moiety of Formula I or the glucose or N-acetylglucosamine moiety of Formula II in the case where Y=H and through the amino acid or the peptide when Y=amino acid or peptide. A sample to be tested for *H. pylori* is contacted with the bound compound of Formula I or Formula II. Bound *H. pylori* may be detected by standard means such as labeled antibodies.

Other features of the invention will become apparent in the course of the following descriptions of exemplary embodiments which are given for illustration of the invention and are not intended to be limiting thereof.

EXAMPLE 1

Synthesis of tetrasaccharide NANα2-3 Gal β1-3NANα2-6)GalNAc

An aqueous solution of equimolar equivalents of galNAc and UDP-gal is stirred at 40° C. in the presence of a β1-3 galactosyltransferase for a sufficient time to effect coupling of the two moieties. The β1-3 galactosyltransferase is isolated from porcine submaxillary glands. Next, three molar equivalents of CMP-NAN are introduced along with an α2-6 sialyltransferase, to form the monosialo compound. Finally an α2-3 sialyltransferase is introduced in the presence of three more equivalents of CMP-NAN to form the tetrasaccharide.

EXAMPLE 2

Synthesis of glycopeptidesaccharide NANα2-3 Gal β1-3NANα2-6) GalNAcβ1-Serine

An aqueous solution of equimolar equivalents of galNAc O-linked to serine and UDP-gal is stirred at 40° C. in the presence of a β1-3 galactosyltransferase for a sufficient time to effect coupling of the two moieties. The β1-3 galactosyltransferase is isolated from porcine submaxillary glands. Next three molar equivalents of CMP-NAN are introduced along with an α2-6 sialyltransferase to form the monosialo compound. Finally an α2-3 sialyltransferase is introduced in the presence of three more equivalents of CMP-NAN to form the glycopeptidesaccharide.

EXAMPLE 3

An anti-Helicobacter composition is prepared by mixing 100 mg of the tetrasaccharide of Example 1 with 250 mg of the $H_2$ receptor antagonist ranitidine. The mixture is then suspended in a mixture of water and propylene glycol.

EXAMPLE 4

An anti-Helicobacter composition is prepared by mixing 100 mg of the tetrasaccharide of Example 1 with 250 mg of the proton pump inhibitor omeprazole. The mixture is then suspended in a mixture of water and propylene glycol.

EXAMPLE 5

An anti-Helicobacter composition is prepared by mixing 100 mg of the tetrasaccharide of Example 1 with 250 mg of a combination of metronidazole, tetracycline, and amoxicillin. The mixture is then suspended in a mixture of water and propylene glycol.

EXAMPLE 6

As a therapeutic treatment, a patient infected with *H. pylori* is treated with the composition of Example 3. The patient is treated orally four times daily with each dosage providing an effective stomach concentration of 100 μg/ml. Therapy is continued for two weeks, after which examination showed eradication of the *H. pylori* bacteria. After eradication, maintenance therapy with the composition of the present invention is continued to prevent recurrence.

EXAMPLE 7

Synthesis of tetrasaccharide NANα2-3 Gal β1-4(NANα2-6)GlcNAc

An aqueous solution of equimolar equivalents of glcNAc and UDP-gal is stirred at 40° C. in the presence of a β1-4 galactosyltransferase for a sufficient time to effect coupling of the two moieties. The β1-4 galactosyltransferase is isolated from porcine submaxillary glands. Next three molar equivalents of CMP-NAN are introduced along with an α2-6 sialyltransferase, to form the monosialo compound. Finally an α2-3 sialyltransferase is introduced in the presence of three more equivalents of CMP-NAN to form the tetrasaccharide.

EXAMPLE 8

Synthesis of tetrasaccharide NANα2-3 Gal β1-3NANα2-6)GlcNAc

An aqueous solution of equimolar equivalents of glcNAc and UDP-gal is stirred at 40° C. in the presence of a β1-3 galactosyltransferase for a sufficient time to effect coupling of the two moieties. The β1-3 galactosyltransferase is isolated from porcine submaxillary glands. Next three molar equivalents of CMP-NAN are introduced along with an α2-6 sialyltransferase, to form the monosialo compound. Finally an α2-3 sialyltransferase is introduced in the presence of three more equivalents of CMP-NAN to form the tetrasaccharide.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A composition comprising, in association with a carrier or excipient suitable for enteral administration, an amount effective to inhibit binding of *Helicobacter pylori* to gastric and duodenal cells, of a composition comprising an oligosaccharide selected from the group consisting of Formula I

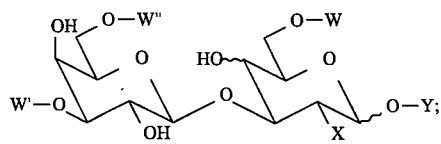

-continued

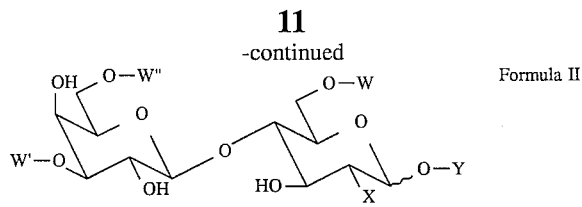

Formula II or a mixture thereof;
wherein:
X is independently OH or NHAc;
Y is independently H, or an amino acid or a peptide of 2–100 amino acids; and
W, W', and W'' are each independently H or

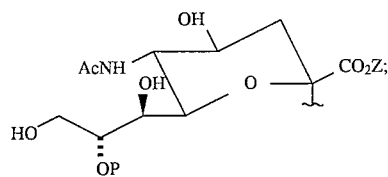

where Z is independently H or a pharmaceutically acceptable cation; and P is independently H or

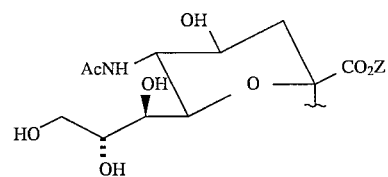

where Z is defined as above;
wherein at least one of W, W' or W'' is an α-N-acetylneuraminic acid moiety, and
wherein W' and W'' are not simultaneously an α-N-acetylneuraminic acid moiety
with the proviso that the compound of Formula II is not NAN α(2→3) Galβ1–4 Glu or NAN α(2→6) Gal β1–4 Glu
wherein a plurality of molecules of said oligosaccharide are each covalently bonded to a pharmaceutically acceptable polymer via the free anomeric carbon of the galactose, N-acetylgalactosamine, glucose or N-acetylglucosamine moiety of Formula I or the glucose or N-acetylglucosamine moiety of Formula II when Y is H or via the amino acid or the 2 to 100 amino acids-long peptide moiety when Y is an amino acid or a 2 to 100 amino acids-long peptide.

2. The composition of claim 1, further comprising an amount effective for H2 blocking of an H2 blocker.

3. The composition of claim 2 wherein said H2 blocker is selected from the group consisting of cimetidine, octreotide, enterogastrone, ranitidine, nizatidine and famotidine.

4. The composition of claim 1, further comprising an antiulcerative amount of an antiulcerative compound.

5. The composition of claim 1, further comprising a proton pump inhibiting amount of a proton pump inhibitor.

6. The composition of claim 5, wherein said proton pump inhibitor is omeprazole.

7. The composition of claim 1, further comprising an antibiotic effective amount of an antibiotic effective against *H. pylori*.

8. The composition of claim 7, wherein said antibiotic is selected from the group consisting of metronidazole, tetracycline, bismuth, erythromycin, macrolide, quinoline, amoxicillin and a mixture thereof.

9. A solid composition according to claim 1.
10. A liquid composition according to claim 1.
11. The composition of claim 1, wherein X is OH.
12. The composition of claim 1, wherein X is NHAc.
13. The composition of claim 1, wherein Y is H.
14. The composition of claim 1, wherein Y is an amino acid or 2 to 100 amino acids-long peptide.
15. The composition of claim 14, wherein Y is a peptide of from 2 to 20 amino acids.
16. The composition of claim 1, wherein at least one of Z is H.
17. The composition of claim 1, wherein at least one of Z is a pharmaceutically acceptable cation.
18. The composition of claim 1, wherein said pharmaceutically acceptable polymer is a polymer is a polylysine, a polyacrylamide or a cyclodextrin.
19. A method of eliminating *Helicobacter pylori* from the stomach or duodenum of a patient in need thereof, comprising administering to said patient an *Helicobacter pylori* eliminating effective amount of composition comprising an oligosaccharide selected from the group consisting of Formula I

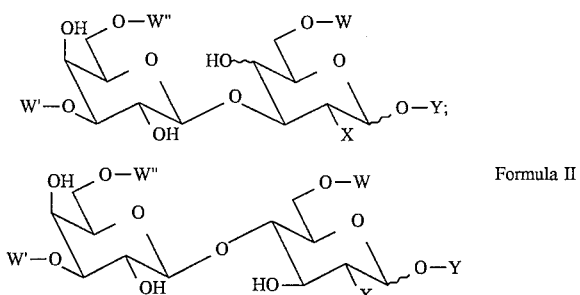

Formula II or a mixture thereof;
wherein:
X is independently OH or NHAc;
Y is independently H, or an amino acid or a peptide of 2–100, amino acids; and W, W', and W'' are each independently H or

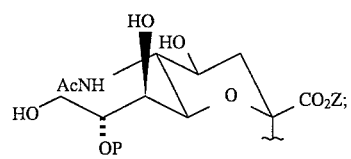

where Z is independently H or a pharmaceutically acceptable cation; and
P is independently H or

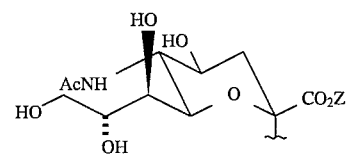

where Z is defined as above;
wherein at least one of W, W' or W'' is an α-N-acetylneuraminic acid moiety, and
wherein W' and W'' are not simultaneously an α-N-acetylneuraminic acid moiety
with the proviso that the compound of Formula II is not NAN α(2→3)Gal β1–4 Glu or NAN α(2→6)Gal 1–4 Glu wherein a plurality of molecules of said oligosaccharide are each covalently bonded to a pharmaceutically acceptable polymer via the free anomeric carbon of the galactose, N-acetylgalactosamine, glucose, or N-acetylglucosamine moiety of Formula I or the glucose or N-acetylglucosamine moiety of Formula II when Y is H or via the amino acid or the 2 to 100 amino acids-long peptide moiety when Y is an amino acid or a 2 to 100 amino acids-long peptide.

* * * * *